United States Patent [19]

Gordon et al.

[11] 4,455,139

[45] Jun. 19, 1984

[54] INTRAVENOUS LIQUID LEVELING DEVICE

[75] Inventors: Marvin Gordon, East Windsor; Joseph Lichtenstein, Colonia; Stephen Kocanowski, Middlesex, all of N.J.

[73] Assignee: Whitman Medical Corporation, Clark, N.J.

[21] Appl. No.: 360,994

[22] Filed: Mar. 23, 1982

[51] Int. Cl.³ .............................................. A61M 5/14
[52] U.S. Cl. .................................... 604/247; 222/58; 137/408
[58] Field of Search ............... 604/246, 248, 247; 137/408, 407; 222/58; 254/325, 394, 398

[56] References Cited

U.S. PATENT DOCUMENTS 2,771,878 11/1956 Rolland et al. ................. 604/248
3,242,924 3/1966 Kraft et al. ...................... 137/408 X
4,137,915 2/1979 Kamen ............................ 222/58

FOREIGN PATENT DOCUMENTS 179306 10/1886 France ............................ 604/248

Primary Examiner—Stephen C. Pellegrino
Attorney, Agent, or Firm—Holman & Stern

[57] ABSTRACT

The surface of the intravenous liquid in a container is maintained at substantially constant height above the patient by suspending the container from an elastic member which stretches along an axis other than the suspension axis for the container. In this manner, the total vertical length of the intravenous unit, including the container, the elastic member and the support hook, is minimized. In a particular embodiment the elastic member is a spring oriented substantially horizontal and combined with a pulley and idler roller to redirect the suspension cord for the intravenous liquid container. In another embodiment the spring is disposed vertically along an axis parallel to the suspension axis. An alarm circuit includes one or more micro switches which are actuated by the moveable spring-attached pulley to provide an audible or visible alarm indication when the suspension spring retracts to a specified position, thereby indicating that the intravenous container is approaching an empty condition.

19 Claims, 12 Drawing Figures

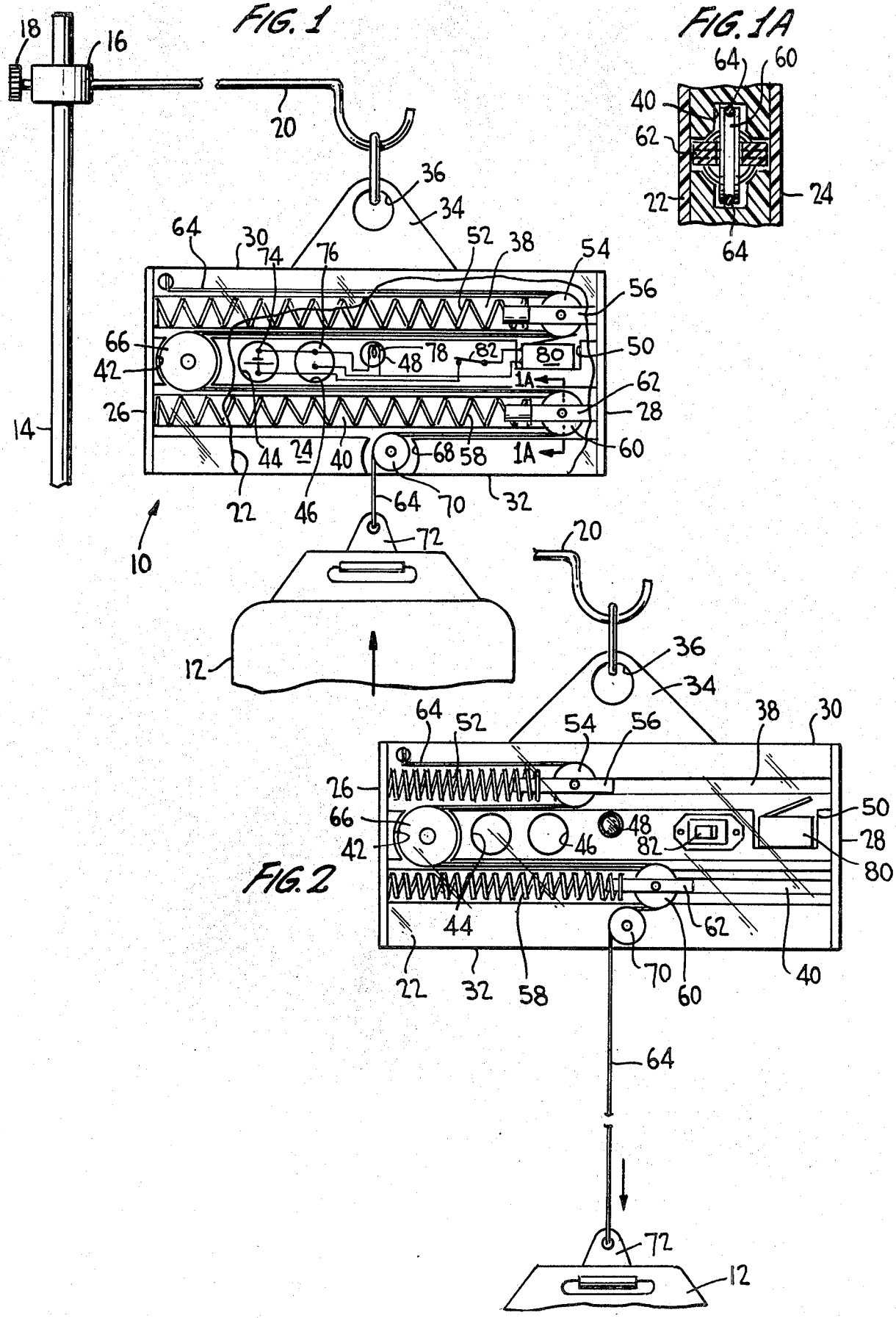

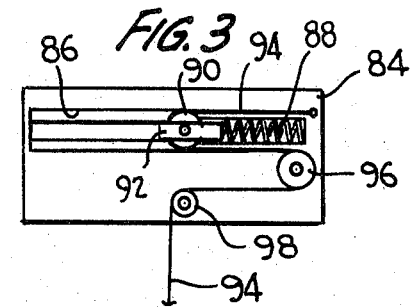
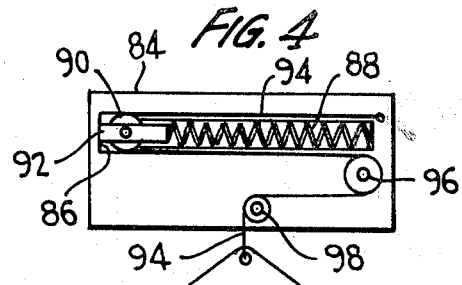
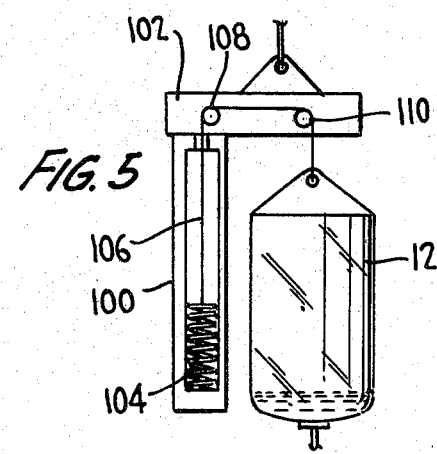
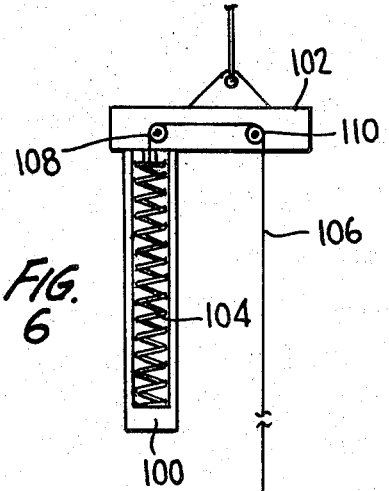
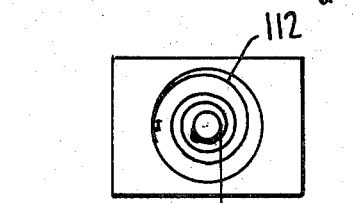
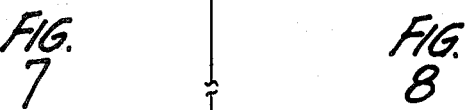
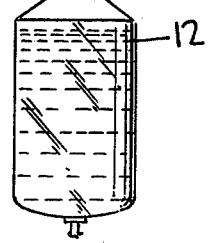

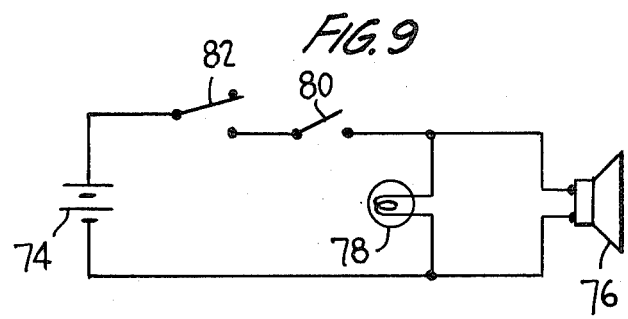
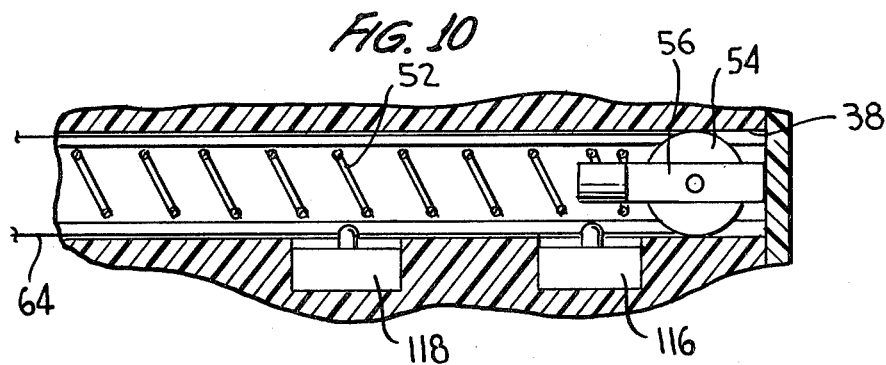
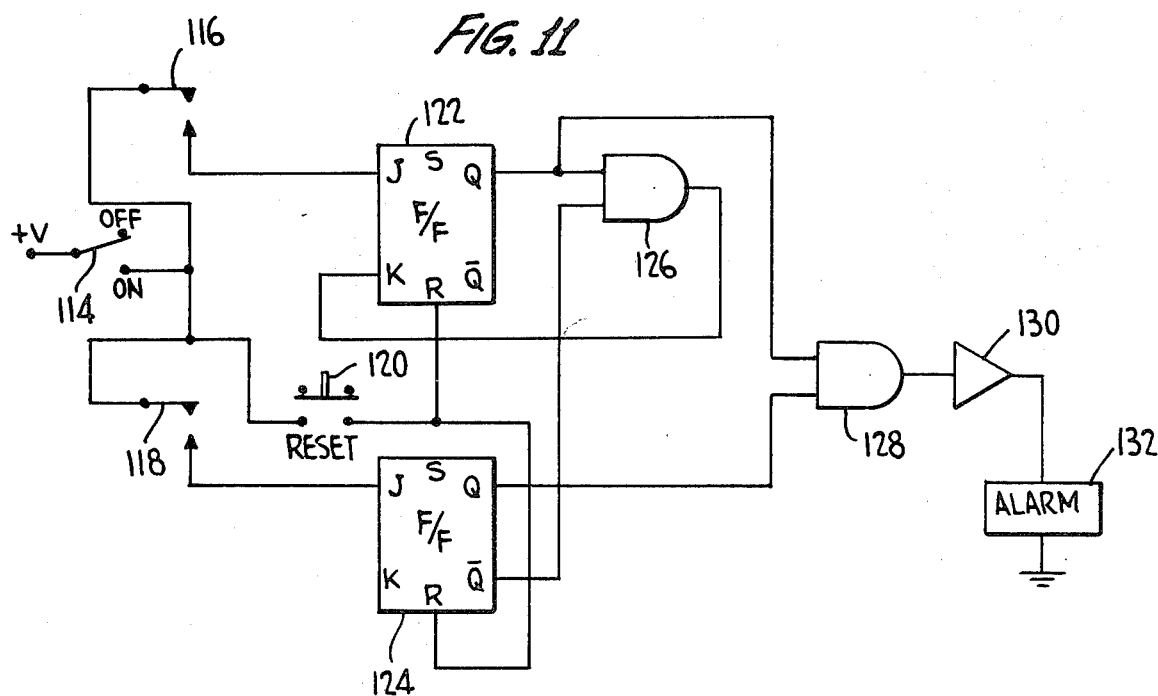

INTRAVENOUS LIQUID LEVELING DEVICE

TECHNICAL FIELD

The present invention relates to intravenous infusion and transfusion apparatus of the gravity-feed type and, more particularly, to apparatus for reducing variations in the flow rate of infusion liquid caused by changes in the height of the liquid column as the amount of liquid in the container decreases.

BACKGROUND OF THE INVENTION

Typically, gravity-feed intravenous administration apparatus includes a container for the liquid to be administered, a tube or conduit connected to the container for conducting the liquid to a hollow needle, and a control device connected in the conduit for controlling the rate of flow of liquid into the patient's vascular system. The control device generally takes the form of an adjustable clamp on the flexible conduit and includes a drip chamber to provide a visual indication of the rate at which the liquid is being administered. Such gravity-feed systems are useful for both infusion, wherein liquid such as glucose, salt solutions, etc., are administered and transfusions, wherein blood is administered. The present invention relates to both processes.

In the administration of intravenous fluids to a patient, controlling the flow rate of the liquid is of critical importance. A patient can suffer serious consequences should the amount of liquid received in a particular period of time exceed a safe limit. The flow rate depends, among other things, upon the difference in height between the top of the liquid in the bottle or flexible bag and the insertion point of the canula usually positioned in the patient's arm. Increasing that distance provides a greater hydrostatic pressure and increases the flow rate. The height of the top of the liquid above the patient varies as the contents of the liquid container decrases. This change in the height of the liquid results in a change of the flow rate. The present invention is concerned with minimizing the flow rate variation caused by changes in the amount of liquid in the container.

A prior art approach to this problem is found in U.S. Pat. No. 2,771,878 to Folland, et al. In this approach, instead of suspending the liquid container directly from a fixed support, the container is supported from a rigid vertically-extending rod which is secured to one end of a compression-type helically-wound cylindrical spring in a cylinder. The spring is calibrated so as to raise the container as a function of the cylinder and its liquid contents, whereby the top of the liquid in the container is maintained at a substantially constant height above the patient. While in theory this system operates as intended, it suffers from some practical disadvantages. Specifically, according to present standards, the bottom of an intravenous (I.V.) liquid container should be disposed approximately three feet above the point of infusion in a patient's arm. A bed-ridden patient's arm is typically disposed approximately two and one half feet above the floor. The commonly-used I.V. bottle has approximately six to ten inches of liquid therein. The total height from which a common gravity-feed system support hook must be located is therefore between six and six and one half feet. In the FOLLAND, et al. patent, the vertically compressable spring is interposed between the hook and the I.V. container. The spring is disposed in a cylinder which is approximately one foot long. In addition, the filled I.V. container, when supported from the spring, compresses the spring approximately nine inches. The Folland, et al. device thereby adds one and three quarter feet to the height of the hook which must therefore be disposed eight feet or more above the floor. This has proven to be too high to be reached by the average nurse whose height is less than five and one half feet.

It is also desirable to provide an alarm indication when the liquid contents of the I.V. container approach empty in order to avoid undesirable consequences from infusing air into the bloodstream. The present invention is concerned with providing a suitable alarm device of this type.

SUMMARY OF THE INVENTION

It is an object of the present invention to provide apparatus which automatically maintains the top of the liquid in an intravenous liquid container at a substantially constant height by adjusting the height of the container as the liquid is emptied from the container, such apparatus being readily installed and removed by medical personnel of even short and average height.

It is another object of the present invention to suspend an intravenous container from a spring so as to maintain the height of the top of the liquid substantially constant and to do so without adding the full length of the spring to the height at which the I.V. container is suspended.

It is still another object of the present invention to provide an automatic alarm indication when a suspended I.V. container is empty or almost empty of its contents.

In accordance with the present invention, a spring, used to support an I.V. container as a function of the weight of contained liquid, is disposed offset from the suspension axis. In one embodiment, one (or more) spring is disposed along a substantially horizontal spring axis and is combined with pulleys and idler rollers to retract a suspension cord off the suspension axis. In another embodiment the spring is disposed along a vertical spring axis oriented parallel to and adjacent the suspension axis. In still another embodiment a coiled spring is employed. An alarm circuit includes one or more microswitches actuated by the moveable spring-attached pulley to provide an audible or visible alarm indication when the suspension spring retracts to a specified position, thereby indicating that the I.V. container is approaching an empty condition.

BRIEF DESCRIPTION OF THE DRAWINGS

The above and still further objects, features and advantages of the present invention will become apparent upon consideration of the following detailed description of one specific embodiment thereof, expecially when taken into consideration with the accompanying drawings, wherein:

FIG. 1 is a front elevation view and plan, partially broken showing a support apparatus of the present invention in its fully retracted position;

FIG. 1A is a view in section taken along lines 1A—1A of FIG. 1;

FIG. 2 is a front elevation view and plan of the embodiment of FIG. 1 as shown in a partially extended position;

FIG. 3 is a front elevation view and plan of another suspension apparatus according to the present invention shown in its extended position;

FIG. 4 is a front elevation view and plan showing the apparatus of FIG. 3 in its fully retracted position;

FIG. 5 is a front elevation view and plan showing another suspension apparatus of the present invention in its fully retracted position;

FIG. 6 is a front elevation view and plan of the apparatus of FIG. 5 shown as fully extended position;

FIG. 7 is a front elevation view and plan showing another suspension apparatus according to the present invention in its fully extended position;

FIG. 8 is a front elevation view and plan of the apparatus of FIG. 7 shown as fully retracted position;

FIG. 9 is an electrical schematic diagram of one form of an alarm device employed with the embodiment of FIG. 1;

FIG. 10 is a partially exploded view and section of a modified form of the embodiment of FIG. 1 showing the operating switches employed in still another alarm circuit;

FIG. 11 is an electrical schematic diagram of a circuit employing the switches illustrated in FIG. 10.

DESCRIPTION OF THE PREFERRED EMBODIMENTS

Referring specifically to FIG. 1 of the accompanying drawings, a suspension apparatus 10 in accordance with the present invention is shown suspending a container 12 of intravenous (I.V.) liquid. Suspension apparatus 10 is self-suspended from a conventional I.V. support stand including vertical post 14, collar 16 which is adjustable in its vertical position on post 14, a locking screw 18 for collar 16 and an arm 20 which extends vertically from collar 16 and terminates in a hook from which element 10 is suspended. Suspension apparatus 10 is illustrated as being formed from transparent plastic material; it is to be understood, however, that any rigid material can be employed instead. Suspension apparatus 10 includes a front wall 22, a rear wall 24, side walls 26 and 28, and top and bottom walls 30 and 32, respectively. Some of these walls may be integrally formed with one another or may simply be secured together by means of adhesive or the like in order to form an enclosed frame within which the components of the suspension apparatus 10 are disposed. A support member 34 projects upwardly from top wall 30 and is provided with an aperture 36 by means of which the support member 10 can be suspended from the distal hook at the end of support arm 20.

The mutually facing interior surfaces of front wall 22 and rear wall 24 are provided with a plurality of recesses and channels so as to define prescribed enclosed regions in which the various components reside. Specifically, an enclosed channel 38 is defined between walls 22 and 24 and extends longitudinally in a horizontal direction when suspension apparatus 10 is supported from support arm 20. In the embodiment illustrated in FIG. 1, channel 38 extends along substantially the entire length of the walls 22 and 24. A similar channel 40 is defined parallel to and below channel 38. A generally circular channel 42 is defined at one end of apparatus 10 between the two elongated channels 38 and 40. The top and bottom of generally circular channel 42 are open for purposes to be described below. Successive spaced circular channels 44, 46 and 48 are defined between the elongated channels 38 and 40 at successive locations from left to right, as viewed in FIG. 1, from channel 42. At the opposite end of walls 22, 24, also between elongated channels 38 and 40, there is defined a generally rectangular channel 50. The upper end of channel 50 opens into one end of the elongated channel 38.

A helically-wound cylindrical compression spring 52 is disposed within elongated channel 38. A pulley assembly 54 is secured to the end of spring 52 which resides approximate the open-top channel 50. In its fully extended condition, spring 52 has one end in contact with side wall 26 and the other end extended so that the pulley assembly 54 bores against the opposite end wall 28. The pulley assembly includes a U-shaped bracket 56 which has a base portion comprising the end-most part of the pulley assembly and two arms which extend along opposite surfaces of the pulley. The two extending arms of the bracket 56 are secured through the pulley center and provide low-friction slide members which guide the pulley assembly 54 through channel 38 as spring 52 is compressed and extended. A similar arrangement, comprising spring 58, pulley assembly 60 and bracket 62, is disposed in channel 40, it being noted that pulley assemblies 60 and 54 are normally disposed at the same end of suspension apparatus 10 when the springs 52 and 58 are fully extended. The cross-sectional view in FIG. 1A illustrates the manner in which the bracket 62 serves as a guide to permit translation of the pulley assembly 60 through channel 40 as spring 58 compresses and expands. In this regard, it is noted that the channel 40 is expanded to accommodate the arms of the bracket member 62 in slidable relation.

Above channel 38, proximate the end of that channel remote from pulley 54, a cord 64 or similar cord-like member is secured to the frame by means of a screw about which the cord wrapped or other similar mechanism for positionally fixing the cord. The cord 64 extends through the upper portion of channel 38 longitudinally so as to extend around the pulley and then back along the lower portion of channel 38. The cord extends into channel 42 and around an idler roller 66 disposed in that channel and serving to change the direction of the cord 64 by 180°. The cord projects into the upper portion of channel 40 and extends longitudinally therealong until it passes over pulley 60. The cord in passing over pulley 60 is re-directed by 180° so that it can pass along the bottom portion of channel 40 until reaching a further generally circular channel 68 defined in the assembly below channel 40. The top of channel 68 is open to receive cord 64 from channel 40; the bottom of channel 68 is also open so as to permit the cord to be wrapped about an idler roller 70 captured in channel 68 and serving to permit the cord 64 to be suspended vertically downward from bottom wall 32 of the suspension apparatus 10. The end of cord 64 which projects from channel 68 is secured to a hook 72 or the like which is adapted to engage the I.V. container 12.

The portion of cord 64 which extends downwardly from apparatus 10 when supporting an I.V. container defines a vertical support axis. It is along this axis that the container 12 acts against spring 52 and 58. More specifically, the position of springs 52 and 58 illustrated in FIG. 1 is the fully expanded position of the springs which is achieved from container 12 is empty. When the container 12 is full, as illustrated in FIG. 2, the added weight of the container causes the flexible elongated cord-like member 64, affixed at one end, to pull both pulleys 54 and 60 to the left (as viewed in FIGS. 1 and 2) so that a greater portion of cord-like member 64 extends along the suspension axis and permits the container 12 to be disposed at a lower level. The degree of compression of springs 52 and 58 depends upon the weight of the contents of I.V. container 12, it being understood that the springs 52 and 58 are shown in FIG. 2 as being substantially fully compressed. In this regard it should be noted that the limit on the degree of compression of spring 58 is determined by the location of channel 68 in which the direction-changing idler roller 70 is disposed. More specifically, pulley 60 cannot be moved to the left beyond idler roller 70 since there is no direction reversing mechanism to the left of idler roller 70 to effect a translational force to the left on pulley 60. By proper calibration of springs 52 and 58, the height of container 12 at any time can be automatically adjusted by the springs to maintain the top of the liquid in container 12 at a substantially constant height above the infusion point in the patient's arm. Thus, suspension apparatus 10 achieves the desirable result of the aforementioned U.S. Pat. No. 2,771,878 (Folland, et al.). However, this result is achieved without the need for inserting the spring along the suspension axis so as to require the suspension apparatus and container to be suspended from an impractical height for most personnel. The general principal envolved in achieving this desirable result is to redirect the suspension cord or cord-like member off of the suspension axis when it is retracted into the suspension apparatus 10. In this regard, it is important that the cord-like member be flexible and elongated and have one point fixed to the frame of the suspension apparatus 10.

It is desirable that the suspension apparatus be provided with an alarm indicator to warn medical personnel when the liquid contents of the I.V. container 12 are approaching empty. This is achieved as part of the present invention by placing a battery 74 in circular chamber 44, an audible alarm device 76 in circular chamber 46 and a lamp 78 in circular chamber 48. In addition, a micro switch 80 is disposed in chamber 50 and has its accuator arm projecting upward into the bottom portion of channel 38 below pulley 54 so as to be contacted and actuated by that pulley when spring 52 is in its fully extended position. An on-off switch 82 is mounted to either the front or rear wall of the assembly and is connected in circuit with the other components in the manner described below. The components 74, 76, 78, 80 and 82 are shown schematically in FIG. 1; these same components are shown pictorially in FIG. 2. The circuit interconnecting these elements is illustrated in FIG. 9 to which reference is now made.

Specifically battery 74 is connected in series circuit with the on-off switch 82, micro switch 80 and the parallel combination of lamp 78 and audible alarm 76. When the on-off switch 82 is closed, both lamp 78 and audible alarm 76 are actuated any time spring 52 is fully extended so as to cause the pulley 54 to close micro switch 80. It should be noted that the purpose of on-off switch 82 is to permit the circuit to be deenergized under the control of personnel so as to prevent the alarms from being actuated during shipment or at times when no I.V. container 12 is suspended from the suspension apparatus 10. It should also be noted that only one of the alarm devices 76, 78 may be provided as desired.

As noted above the advantage of providing a relatively short-length suspension apparatus is achieved by permitting the springs 52, 58 to expand and compress along axes which are not co-axial with the suspension axis of cord 64. This effect need not be achieved with horizontally-extending springs as illustrated in FIGS. 1 and 2 although it is clear that the horizontally-extending springs effect a greater length saving for the over all suspension apparatus than would springs extending diagonally with respect to the vertical. Importantly, however, such diagonally-extending springs could be employed and such employment resides within the scope of the present invention.

It should also be noted that the use of two springs in the embodiment of FIGS. 1 and 2 provide for greater translation of cord-like member 64 along the suspension axis under the weight of the contents of I.V. container 12. However, as illustrated in FIGS. 3 and 4, a single generally horizontally-extending spring may be employed under the scope of the present invention. Specifically, a frame 84 has a generally horizontally-extending channel 86 defined therein, much in the same manner as channels 38 and 40 are defined in apparatus 10 of FIGS. 1 and 2. A helically-wound generally cylindrical compression spring 88 is disposed in channel 86 and has a pulley assembly 90 with its slide bracket 92 secured to one end of the spring. Cord-like member 94 is fixed at one point, proximate the opposite end of channel 86 from a pulley assembly 90, and extends along that channel, around pulley 90, and back along the channel to a direction-changing idler roller or similar member 96. Member 96 turns the cord-like member 94 by 180° so that the cord can pass about a second direction-changing member 98 and then pass vertically out from the frame 84 where it supports the I.V. container 12. The apparatus of FIGS. 3 and 4 is shown with the I.V. container substantially full and therefore spring 88 substantially compressed in FIG. 3; the I.V. container 12 is almost empty so that spring 88 is completely expanded in the FIG. 4 illustration.

In the embodiment of FIGS. 5 and 6, the spring compression and expansion axis is vertically-extending but is disposed parallel to rather than coaxially with the suspension axis for I.V. container 12. Spring 104 is disposed within a generally cylindrical chamber 100 which is secured to a support bracket 102. The support cord or cord-like member 106 extends vertically upward from spring 104, through chamber 100 to a first guide member 108 which is secured to support 102 and re-directs cord 106 by 90°. The cord then passes over another re-direction member 110 so that the cord 106 can be suspended vertically from member 110 and support I.V. container 112 along the suspension axis. The container 12 is shown substantially empty in FIG. 5 and substantially full in FIG. 6. For this embodiment it is noted that spring 104 is a helically-wound generally cylindrical expansion spring rather than a compression spring, meaning that its normal or unstressed position is compressed, as illustrated in FIG. 5, and its stressed position is expanded as illustrated in FIG. 6.

Still another embodiment of the present invention is illustrated in FIGS. 7 and 8 wherein a spiral spring 112 is employed instead of a helically-wound compression or expansion cylindrical spring as in the other embodiments. Operation of the apparatus illustrated in FIGS. 7 and 8 follows from that described above whereby the spiral spring 112 is stressed from the I.V. container 12 suspended therefrom is full and is substantially unstressed when container 12 is empty. The full position is illustrated in FIG. 7 and the substantially empty position is illustrated in FIG. 8.

Referring now to FIG. 11 of the accompanying drawings, a further embodiment of the alarm circuitry for the suspension apparatus of the present invention is illustrated. The purpose of the circuit of FIG. 11 is to prevent the alarm elements from being activated during shipping of the suspension apparatus, during storage of the suspension apparatus and at times when the suspension apparatus is suspended from a conventional I.V. pole without having an I.V. container suspended therefrom. The circuit of FIG. 11 includes an on-off 114 to which a source of voltage is connected. The normally open contact of switch 114 has three parallel circuits extending therefrom including a first micro switch 116, a second micro switch 118 and a manually actuable reset switch 120. The normally open contact of micro switch 116 is connected to the J input terminal of a flip flop 122. The normally open contact of micro switch 118 is connected to the J input terminal of a further flip flop 124. The normally open contact path of the push button reset switch 120 is connected to the reset input terminal R of each of flip flops 122 and 124. The Q output signal from flip flop 122 is applied as one input signal to a two-input AND gate 126. The other input signal for that AND gate is derived from the $\bar{Q}$ derived from flip flop 124. The output signal from AND gate 126 is fed back to the K input terminal for flip flop 122. A further two-input AND gate 128 receives its input signals from the two Q output signals from flip flop 122 and 124. AND gate 128 feeds a driver amplifier 130 which in turn actuates an alarm unit 132 which may be either an audible or a visible alarm.

Before describing the operation of the circuit of FIG. 11, reference is made to FIG. 10 which shows a modification in channel 38 of the embodiment of FIGS. 1 and 2 which is made to accommodate the improved circuit of FIG. 11. Specifically, micro switches 116 and 118 are placed with their actuator members projecting into channel 38 at respective successive locations along the channel. More specifically, as pulley 54 is retracted by spring 52 into channel 38, it first actuates switch 116 and then actuates switch 118. Thus, when a full I.V. container is suspended from cord-like member 64 at the bottom of assembly 10, pulley assembly 54 actuates switches 116 and 118 in sequence as it passes through channel 38. As the container 12 begins to empty, the pulley moves in the opposite direction under the guiding force of spring 52 and successively operates the micro switches in the inverse order, namely micro switch 118 first and then micro switch 116.

Relating the aforegoing to the circuit of FIG. 11, assume that both flip flops are initially reset by actuation of reset switch 120. Both flip flops 122 and 124 are thus placed in their $\bar{Q}$ state. If a fully loaded I.V. container is suspended from cord 64, micro switch 116 is first actuated so as to trigger flip flop 122 at the J input terminal. This provides a binary one output signal at the Q ative terminal of flip flop 122. This binary one output signal enables AND gate 126 which acts immediately to reset flip flop 122 at its K input terminal. The Q output signal from 122 is therefore immediately switched back to its binary zero state. As pulley 54 passes the second micro switch 118, the flip flop 124 is switched at its J input terminal to provide a binary one Q active signal to AND gate 128. AND gate 128 is thus primed by this signal to await the next actuation of flip flop 122. This occurs as the container 12 gradually empties so that it first passes micro switch 118. This passage past micro switch 118 has virtually no effect since flip flop 124 is already set to provide a binary one Q output signal to AND gate 128. Further emptying of container 12 causes the pulley 54 to pass switch 116 so that flip flop 122 is set. The resulting binary one Q output signal from flip flop 122 enables AND gate 128 so that driver 130 can initiate the alarm signal at alarm unit 132. The alarm continues to ring until such time as the reset switch 120 is actuated, whereby the two flip flops 122 and 124 are reset and the AND gate 128 is disabled.

As described hereinabove, it is not necessary that the resilient forces exerted on the cord-like member 64 be provided by springs; any elastic type element, properly calibrated, can serve the purpose. In addition, it is to be understood that the path to the patients's arm from container 12, which is not illustrated or described herein because it is not part of the present invention, is conventional and would include a suitable flow control device as employed in the prior art.

While we have described and illustrated specific embodiments of our invention, it will be clear that variations of the details of construction which are specifically illustrated and described may be resorted to without departing from the true spirit and scope of the invention defined in the appended claims.

We claim:

1. Apparatus for use in administering intravenous liquid from a container into a patient, which container is suspended from a level above the point of infusion, said liquid being delivered from the container throug a liquid flow path, said apparatus comprising:

a flexible elongated cord-like member for suspending said container for vertical movement along a vertical axis which is at least partially co-extensive with said cord-like member; and resilient means engaged by said cord-like member for selectively diverting varying lengths of said cord-like member from said vertical axis to raise and lower said container as a function of the weight of said container and its liquid contents;

wherein said resilient means comprises:

at least one spring member engaged by said cord-like member so as to elastically vary the length of the spring member as a function of the weight of said container and its liquid contents;

chamber captively containing said spring member so as to restrict the direction of the elastic length variation of the spring member along a further axis which is skewed relative to said vertical axis, wherein said spring member is disposed along said further axis;

direction changing means for guiding said cord-like member to convert length change of said spring member along said further axis to a vertical movement of said cord-like member along said vertical axis.

2. The apparatus according to claim 1 wherein said direction changing means comprising at least one idler roller.

3. The apparatus according to claim 1;

wherein said spring member is a helically-wound compression spring having a pulley secured to one end thereof, said pulley being captively secured for movement along said further axis in said chamber along with said one end of said compression spring;

wherein said chamber is defined in a frame member;

wherein said cord-like member is secured at one point along its length to said frame member and extends through said chamber in a first direction, around said pulley, and back through said chamber in another direction opposite said first direction to engage said direction-changing means.

4. The apparatus according to claim 3 wherein said further axis is substantially horizontal.

5. The apparatus according to claim 1 wherein said resilient means comprises:
a frame member;
first and second generally elongated chambers extending along first and second respective axes skewed to said vertical axis;
first and second helically-wound compression springs captively positioned in said first and second chambers, respectively, concentrically about said first and second axes, respectively;
a first pulley secured to one end of said first spring and captively secured in said first chamber to be moveable along only said first axis with said one end of said first chamber;
a second pulley secured to one end of said second spring and captively secured in said second chamber to be moveable along said second axis along with one end of said second spring;
wherein said cord-like member is secured to said frame member and extends through said first chamber in one direction parallel to said first axis, around said first pulley and back through said first chamber and in an opposite direction parallel to said first axis, through said second chamber in a first direction parallel to said second axis, around said second pulley and back through said second chamber in an opposite direction along said second axis; and
direction-changing means secured to said frame for guiding said cord-like member, after it passes through said second chamber in said opposite direction, to convert compression of said first and second springs along said first and second axes respectively to vertical movement of said cord-like member along said vertical axis.

6. The apparatus according to claim 5 further comprising guide means, secured to said frame member between said first and second chambers, for guiding said cord-like member between said chambers.

7. The apparatus according claim 5 or 6 wherein said first and second axes are horizontal.

8. The apparatus according to claims 5 or 6 wherein said first and second chambers are substantially parallel and co-extensive in length.

9. The apparatus according to claim 5 further comprising indicator means for providing an indication signal in response to said container being raised to a predetermined height above said patient by said resilient means along said vertical axis, said indicator means comprising:
a battery mounted in said frame member;
an indicator mounted in said frame member;
a micro switch mounted in said frame member and including an actuator disposed in one of said chambers so as to be actuated by the pulley in that chamber when the spring in that chamber is fully extended; and
means connecting said battery, said indicator and said switch in a series circuit.

10. Apparatus for use in administering intravenous liquid from a container into a patient, which container is suspended from a level above the point of infusion, said liquid being delivered from the container through a liquid flow path, said apparatus comprising:
a flexible elongated cord-like member for suspending said container for vertical movement along a vertical axis which is at least partially co-extensive with said cord-like member; and
resilient means engaged by said cord-like member for selectively diverting varying lengths of said cord-like member from said vertical axis to raise and lower said container as a function of the weight of said container and its liquid contents;
wherein resilient means comprises:
at least one spring member engaged by said cord-like member so as to elastically vary the spring member length as a function of the weight of said container and its liquid contents;
a chamber captively containing said spring member so as to restrict the direction of its elascit length variation along a further axis which is substantially parallel to said vertical axis, wherein said spring member is disposed along said further axis; and
direction-changing means for guiding said cord-like member through a 180° direction change to convert elastic length variation of said spring member in one vertical direction to vertical movement of said cord-like member in said container in an opposite vertical direction.

11. The apparatus according to claims 1, 3, 5 or 10 further comprising:
indicator means for providing an indicator signal in response to said container being raised to a predetermined height above said patient by said resilient means.

12. The apparatus according to claim 11 wherein said indicator signal is an audible alarm signal.

13. The apparatus according to claim 11 wherein said indicator signal is a visible alarm signal.

14. Apparatus for use in administering intravenous liquid from a container into a patient, which container is suspended from a level above the point of infusion into the patient, said liquid being delivered from the container through a liquid flow path, said apparatus comprising:
a flexible elongated cord-like member having first and second spaced points of attachment, said first point being secured to said container to suspend said container for vertical movement along a longitudinal axis coaxially disposed with at least part of said cord-like member; and
a flow rate stabilizing means to which said second point of attachment is secured for automatically maintaining the upper surface of liquid in said container at a substantially constant height above the patient by raising and lowering the container as a function of the weight of said container and said liquid, said flow rate stabilizing means comprising resilient means engaged by said cord-like member between said first and second points of attachment of said cord-like member for selectively diverting varying lengths of said cord-like member from said vertical axis as a function of the weight of said liquid container and its contents;
wherein said resilient means comprises:
at least one spring member engaged by said cord-like member so as to elastically vary the length of the spring member as a function of the weight of said container and its contents;

a chamber captively containing said spring member so as to restrict the direction of the elastic length variation of the spring member along a further axis which is skewed relative to said vertical axis, wherein said spring member is disposed along said further axis; and direction changing means for guiding said cord-like member to convert length change of said spring member along said further axis to vertical movement of said cord-like member along said vertical axis.

15. The apparatus according to claim 14 wherein said further axis is substantially horizontal.

16. Apparatus for use in administering intravenous liquid from a container into a patient, which container is suspended from a level above the point of infusion into the patient, said liquid being delivered from the container through a liquid flow path, said apparatus comprising:

a flexible elongated cord-like member having first and second spaced points of attachment, said first point being secured to said container to suspend said container for vertical movement along a longitudinal axis coaxially disposed with at least part of said cord-like member; and a flow rate stabilizing means to which said second point of attachment is secured for automatically maintaining the upper surface of liquid in said container at a substantially constant height above the patient by raising and lowering the container as a function of the weight of said container and said liquid, said flow rate stabilizing means comprising resilient means engaged by said cord-like member between said first and second points of attachment of said cord-like member for selectively diverting varying lengths of said cord-like member from said vertical axis as a function of the weight of said liquid container and its contents;

wherein said resilient means comprises:

a frame member;

first and second generally elongated chambers extending along first and second respective axes skewed to said vertical axis;

first and second helically-wound compression springs captively positioned in said first and second chambers, respectively, concentrically about said first and second axes respectively;

a first pulley secured to one end of said first spring and captively secured in said first chamber to be moveable along only said first axis with said one end of said first spring;

a second pulley secured to said one end of said second spring and captively secured in said second chamber to be moveable only along said second axis with said one end of said second spring;

wherein said cord-like member is secured at said second attachment point to said frame member and extends to said first chamber in one direction parallel to said first axis, around said first pulley and back to said first chamber in an opposite direction parallel to said first axis, through said second axis, around said second pulley and back through said second chamber in an opposite direction along said second axis; and direction changing means secured to said frame for guiding said cord-like member, after it passes through said second chamber in said opposite direction, to convert compression of said first and second springs along with first and second axes, respectively, to vertical movement of said cord-like member along said vertical axis.

17. The apparatus according to claims 15 or 16 further comprising indicator means for providing an indication signal in response to said container being raised to a predetermined height above said patient by said resilient means.

18. The apparatus according to claim 17 wherein said indication signal is an audible alarm signal.

19. The apparatus according to claim 17 wherein said indication signal is a visible alarm signal.

* * * * *